United States Patent
Rini et al.

(10) Patent No.: US 11,207,472 B2
(45) Date of Patent: Dec. 28, 2021

(54) PEN NEEDLE ASSEMBLY

(71) Applicant: Becton, Dickinson and Company, Franklin Lakes, NJ (US)

(72) Inventors: Christopher Rini, Raleigh, NC (US); Richard Klug, Roxboro, NC (US); Ronald Pettis, Cary, NC (US); David Huang, Hayward, CA (US); Shresta Marigowda, Morton, PA (US); Todd Sack, Dover, DE (US); Mark Bowen, Stow, MA (US); Matthew Zuschlag, Randolph, NJ (US); David Schiff, Highland Park, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 645 days.

(21) Appl. No.: 16/073,709

(22) PCT Filed: Apr. 14, 2016

(86) PCT No.: PCT/US2016/027577
§ 371 (c)(1),
(2) Date: Jul. 27, 2018

(87) PCT Pub. No.: WO2017/131802
PCT Pub. Date: Aug. 3, 2017

(65) Prior Publication Data
US 2021/0100960 A1    Apr. 8, 2021

Related U.S. Application Data

(63) Continuation-in-part of application No. PCT/US2016/015680, filed on Jan. 29, 2016, and a
(Continued)

(51) Int. Cl.
*A61M 5/32* (2006.01)
*A61M 5/46* (2006.01)
*A61M 5/34* (2006.01)

(52) U.S. Cl.
CPC ............ *A61M 5/46* (2013.01); *A61M 5/3202* (2013.01); *A61M 5/3293* (2013.01); *A61M 5/34* (2013.01); *A61M 5/343* (2013.01); *A61M 5/349* (2013.01)

(58) Field of Classification Search
CPC . A61M 5/3202; A61M 5/3213; A61M 5/3293
See application file for complete search history.

(56) References Cited

U.S. PATENT DOCUMENTS 3,662,753 A * 5/1972 Tassell .................. A61M 5/348
604/89
4,040,421 A   8/1977 Young
(Continued)

FOREIGN PATENT DOCUMENTS

CN    102395396 A    3/2012
JP    S53-142088 A    12/1978
(Continued)

OTHER PUBLICATIONS

Chinese Office Action dated Apr. 2, 2021, which issued in the corresponding Chinese Patent Application No. 201680001274.X, including Eng. translation.

*Primary Examiner* — Laura A Bouchelle
(74) *Attorney, Agent, or Firm* — Dickinson Wright PLLC

(57) ABSTRACT

A needle hub assembly for a pen needle includes a needle hub, an inner shield and an outer cover. The open end of the outer cover is closed by a removable seal to access the needle hub. The needle hub has a body with a shoulder and a tower extending from the body for supporting a cannula. The inner shield fits over the tower and the cannula and includes a flange that has an outer dimension complement-
(Continued)

ing the outer dimension of the needle hub and contacts the shoulder of the needle hub in the assembled condition. The outer cover encloses the needle hub and the inner shield and includes a stop member on an inner surface that contacts the flange of the inner shield to capture the inner shield between the shoulder of the needle hub and the outer cover.

19 Claims, 13 Drawing Sheets

Related U.S. Application Data continuation-in-part of application No. PCT/US2014/068498, filed on Dec. 4, 2014.

(56) References Cited

U.S. PATENT DOCUMENTS

| | | |
|---|---|---|
| 4,125,588 A | 11/1978 | Hansen et al. |
| 5,741,236 A * | 4/1998 | Kakiuti ............... A61M 5/001 604/192 |
| 5,941,857 A * | 8/1999 | Nguyen ............. A61M 5/3205 604/263 |
| 6,843,781 B2 | 1/2005 | Alchas et al. |
| 8,133,202 B2 * | 3/2012 | Marsh ................. A61M 5/002 604/117 |
| 2007/0293819 A1 | 12/2007 | Giambattista et al. |
| 2009/0069753 A1 | 3/2009 | Ruan et al. |
| 2009/0069755 A1 * | 3/2009 | Horvath ............. A61M 5/3293 604/240 |
| 2011/0118667 A1 | 5/2011 | Zaiken et al. |
| 2012/0071835 A1 | 3/2012 | Marshall et al. |
| 2012/0109052 A1 | 5/2012 | Wei et al. |
| 2012/0191046 A1 | 7/2012 | Larsen et al. |
| 2014/0343507 A1 | 11/2014 | Karlsson et al. |
| 2015/0297837 A1 | 10/2015 | Schraga |
| 2017/0197039 A1 | 7/2017 | Shiozaki et al. |

FOREIGN PATENT DOCUMENTS

| | | |
|---|---|---|
| JP | H08-299440 A | 11/1996 |
| JP | 2004-504891 A | 2/2004 |
| JP | 2004-305749 A | 11/2004 |
| JP | 2006-517129 A | 7/2006 |
| JP | 2009-090098 A | 4/2009 |
| JP | 2009-90098 A | 4/2009 |
| JP | 2009-101140 A | 5/2009 |
| JP | 2012-519546 A | 8/2012 |
| JP | 2012-519546 A | 8/2012 |
| JP | 2012-523876 A | 10/2012 |
| JP | 2012-529322 A | 11/2012 |
| JP | 2013-138879 A | 7/2013 |
| JP | 5385260 B2 | 10/2013 |
| WO | WO-02100467 A2 | 12/2002 |
| WO | WO-2012085579 A2 | 6/2012 |
| WO | 2014105905 A2 | 7/2014 |
| WO | 2015-186792 A1 | 12/2015 |

* cited by examiner

PEN NEEDLE ASSEMBLY

This application claims priority from International Application No. PCT/US2016/15680, filed on Jan. 29, 2016, and is a continuation-in-part of that application for the United States. This application is also a continuation-in-part of International Application No. PCT/US2014/068498, filed on Dec. 4, 2014, for the United States.

BACKGROUND OF THE INVENTION

Field of the Invention

The present invention is directed to medical devices for injecting a medication to a patient. Specifically the invention is directed to a pen needle including a needle hub with a patient-contacting surface, an inner shield, and an outer cover. The needle hub of the assembly can be installed on a medication pen to administer medications.

Description of the Related Art

A medication pen for delivering self-administered medications generally includes a pen body, which houses a medication compartment, and a separate pen needle which may be attached to and detached from the pen body. The pen needle includes a needle hub having a recess on the proximal side for receiving the pen body and a proximal (non-patient end) needle accessing the medication compartment, typically piercing the septum of a medication cartridge in the pen body. The distal patient end of the pen needle includes the needle or cannula that is inserted into the injection site.

Injections may be performed in the intradermal (ID) region, the subcutaneous (SC) region and the intramuscular (IM) region. For many types of injectable medications, including insulin, the SC region is preferred for administering an injection. See, for example, Lo Presti, et al., Skin and subcutaneous thickness at injecting sites in children with diabetes: ultrasound findings and recommendations for giving injection, *Pediatric Diabetes* (2012).

Shorter needles, such as 4 mm and 5 mm needles, are adapted to achieve injection to a specified target depth in a subcutaneous region. In one aspect, the present invention addresses the need to ensure that a needle is inserted to its target depth, regardless of the angle at which the user may approach the injection site with the medication pen.

In certain prior art pen needles the cannula is supported in an axially positioned post on the needle hub. The post forms a narrow portion extending distally from the relatively wider portion in which the pen body is received. In other pen needles known in the art, a distal face of the needle hub placed against the injection site may have a slight taper at the edge. However, the edge of the needle hub engages the skin when the cannula is inserted at an angle, interfering with the injection. The slight taper is not functional during an injection, or is only at the edge of the distal face of the needle hub, generally having a radius of curvature greater than about 16.0 mm.

While the prior devices are generally suitable for the intended use, there is a continuing need for improved devices for controlling the penetration of a cannula for delivering a drug or medicament.

SUMMARY OF THE INVENTION

The present invention is directed to an injection device and particularly to a needle hub assembly for coupling to an injection pen where the needle hub has a skin contact surface configured for controlling the depth of penetration by a cannula extending from the needle hub. The needle hub has a contact surface with a height and width that complement each other to control the depth of penetration of the cannula.

These and other objects of the invention are achieved in one aspect of the invention by a pen needle assembly having a needle hub with a cannula, an inner shield for covering the cannula and an outer cover the fits over the inner shield and the needle hub.

One feature of the invention is to provide a pen needle hub assembly having a needle hub with a cannula, an inner shield that fits over a top portion of the needle hub to enclose the cannula and an outer cover that fits over the inner shield and needle hub, with a peel tab for closing the open end of the outer cover. The needle hub in one embodiment has a body with a side wall with a top end and a bottom end. The top end of the side wall has an outer surface with a plurality of recesses extending in a longitudinal direction with respect to a central axis of the needle hub, where the recesses form a scalloped shape. The recesses can result in the top end of the side wall with greater flexibility compared to the side wall where no recesses are formed. The recesses cooperate with the outer cover to rotate the needle hub when coupling to and removing from the pen delivery device.

The bottom end of the side wall of the needle hub can have an inner surface with at least one recessed portion so that the bottom end of the wall has a thickness to provide some flexibility similar to or complementing the flexibility of the top end of the side wall. In one embodiment, the recess on the inner surface of the bottom end of the side wall can be continuous and extend around the entire circumference of the side wall at the open end of the needle hub and provide an opening with a dimension to allow easy coupling of the needle hub to the pen needle device.

Another feature of the invention is to provide a needle hub having a body with a side wall, a top surface forming a shoulder extending perpendicular to the central axis of the needle hub, and a tower or upper portion extending upwardly from the top surface a distance to from a contact surface with the skin of the patient during injection. The tower has an end wall with an axial face at a distal end forming the skin contact surface. A supporting post extends inwardly from an inner face of the end wall with a central channel or bore to receive the cannula. The post projects axially into the cavity of the hub a distance to support the cannula. In one embodiment, the inner surface of the end wall has at least one, and typically a plurality of reinforcing ribs, that extend radially between the post and a side wall of the tower.

The inner shield of the invention can have a dimension to fit over the tower of the needle hub to enclose a top portion of the needle hub and enclose the cannula. The inner shield has a body with a side wall having an inner dimension to fit over the tower of the needle hub. An outwardly extending flange extends from a bottom end of the inner shield to contact the top wall of the body of the needle hub to limit the depth of insertion of the needle hub into the inner shield. The flange can have an outer dimension to complement the outer dimension of the body of the needle hub.

In one embodiment of the invention the inner shield has an upper portion extending from the body of the inner shield a distance to enclose the cannula. The outer surface of the inner shield can be provided with one or more griping members projecting outwardly from the side of the upper portion. In one embodiment, the gripping members can be a projecting member with a surface that is inclined with respect to the center axis of the inner shield.

The outer cover of the invention can have a dimension to enclose the inner shield and the needle hub. The inner shield can have a body with a side wall defining an open end of the outer cover. A bottom end of the side wall next to or adjacent the open end has an outwardly extending flange that surrounds the perimeter of the side wall. An inner surface of the side wall has a recess at the open end to provide a space or gap between the inner surface of the outer cover and the needle hub. The bottom end of the side wall can have a beveled or chamfered inner edge.

In one embodiment of the invention, the inner surface of the body of the outer cover has at least one and typically a plurality of radially spaced detents extending into the cavity of the body of the outer cover. The detents can extend in a longitudinal direction with respect the center axis of the outer cover and project inwardly to provide a friction fit of the outer cover to the outer surface of the needle hub. The outer surface of the outer cover can have a plurality of recesses that form the detents on the inner surface. One or more stop members can be formed on the inner surface of the body of the outer cover and provided with a downwardly oriented face for engaging the top end of the needle hub or the inner shield to limit the travel of the needle hub and inner shield into the cavity of the outer cover. In one embodiment, the stop members are formed with one or more of the detents and include a portion extending radially inward a distance to engage the flange on the inner shield.

The needle hub in various embodiments of the invention can have a convex distal axial surface for contacting the skin during needle insertion and drug delivery. The needle hub can have a contact surface area of about 5-50 mm². The contact surface in one embodiment can have a height of about of 0.3 to 0.7 mm and a surface area of 1-4 mm².

The needle hub can have a convex surface with a height of about 0.5 to 6.0 mm and a cannula with a length of about 1-5 mm projecting from the contact surface for penetrating the skin. The cannula can be located in the center of the contact surface so that the contact surface surrounds the cannula. In one embodiment the invention, the convex contact surface can have a height of about 0.5 to 1.0 mm and width of about 5.0 to 7.0 mm to provide sufficient surface area and a suitable shape and angle with respect to the axis of the cannula to contact the skin and provide the controlled depth of penetration by the cannula into the skin. In one embodiment, the cannula can have a length of about 4.2 mm.

It will be understood that each of the preferred or optional features of the various embodiments may be combined with other features and features described in combination with one or more particular features may also be combined with one or more other features of the other embodiments.

These and other features of the invention will become apparent from the following detailed description of the invention, which in conjunction with the drawings disclose various embodiments of the invention.

BRIEF DESCRIPTION OF THE DRAWINGS

The following is a brief description of the drawing in which.

DETAILED DESCRIPTION OF THE INVENTION

Figure 1:
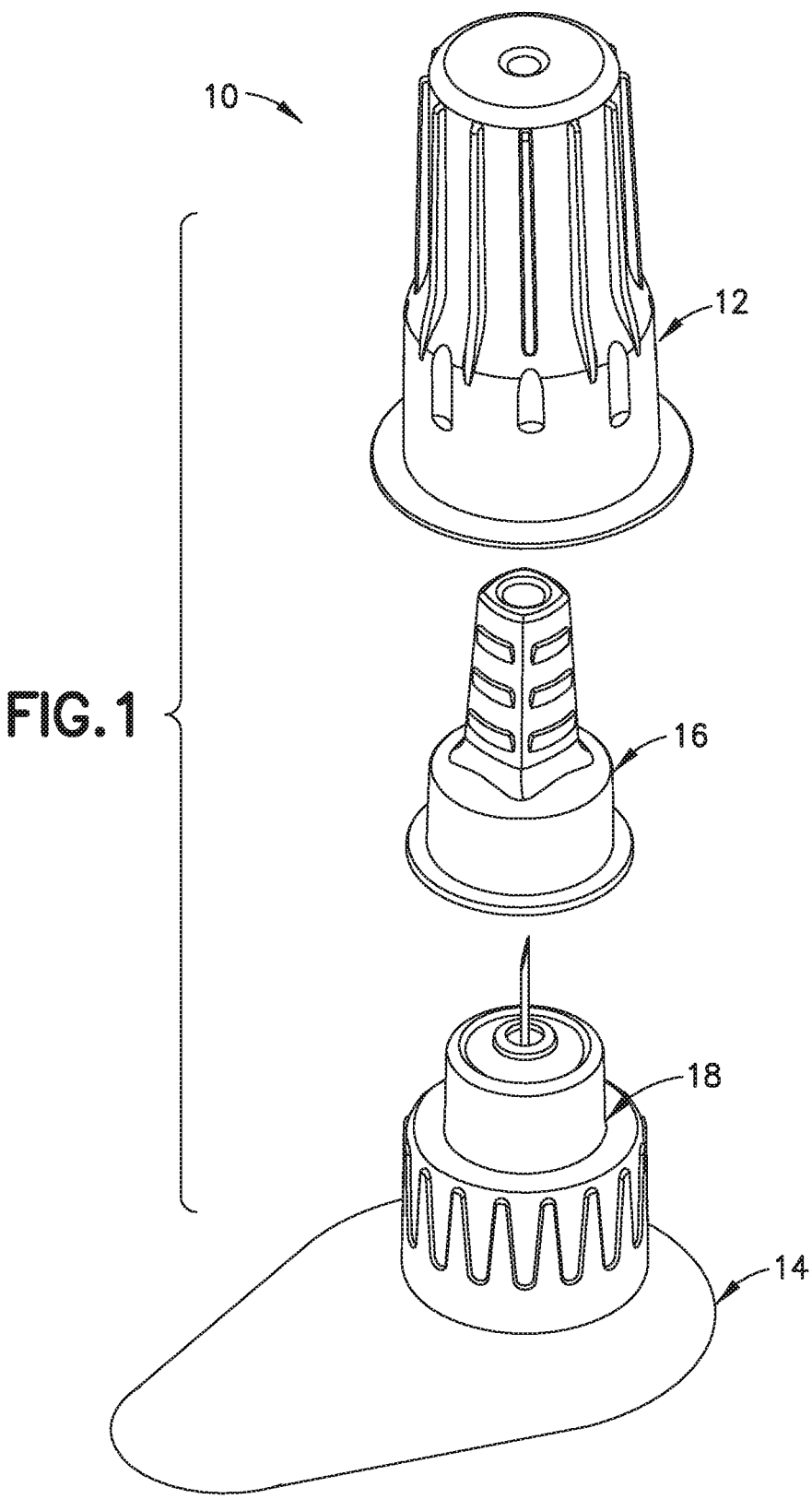
FIG. 1 is an exploded perspective view a needle hub assembly according to an embodiment of the invention.
Figure 2:
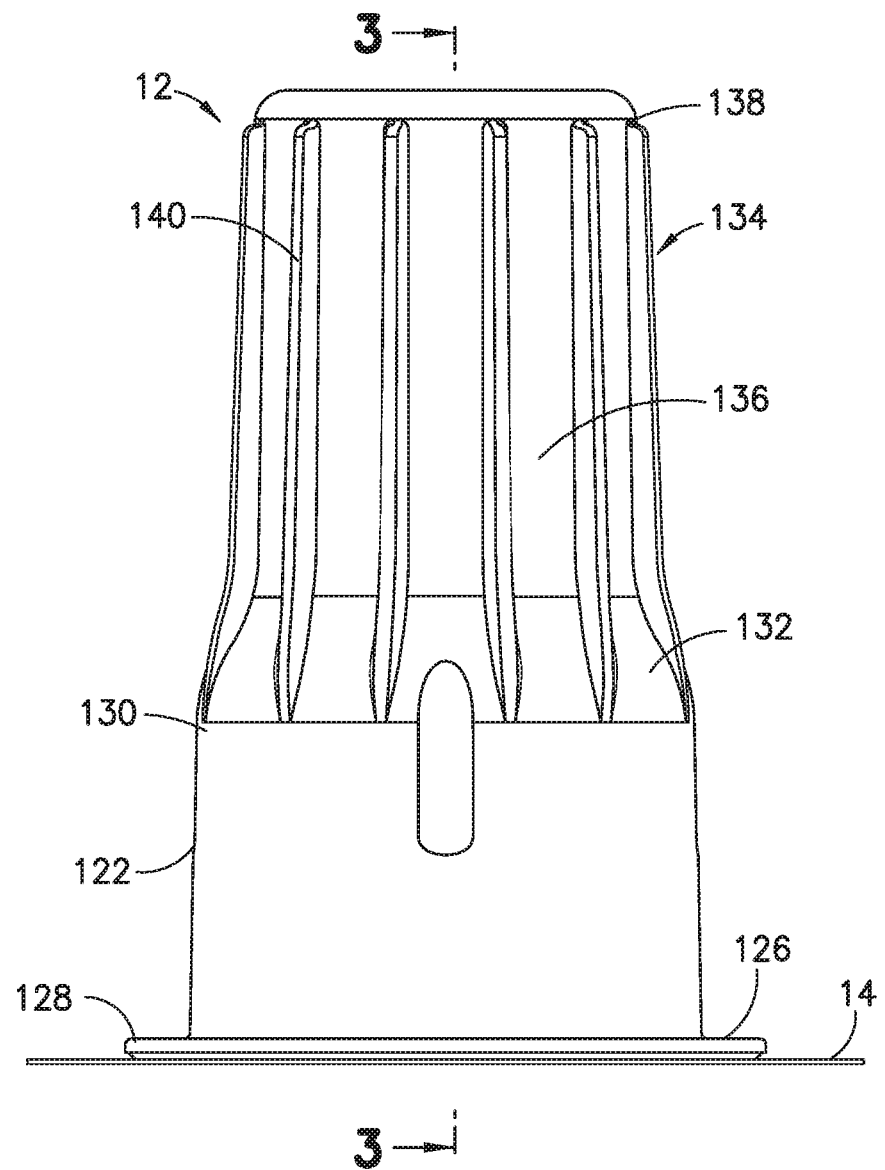
FIG. 2 is a side elevational view of the needle hub assembly of FIG. 1.

A "medication pen" is used herein to refer to a device having a medication compartment, typically containing multiple doses of medication, and a separate pen needle. The phrase "pen needle" refers to a needle-bearing assembly which can be attached to the medication pen body so that a proximal end of the pen needle assembly accesses a medication compartment and a distal end is adapted for insertion into an injection site to perform one or more injections. The terms "needle" and "cannula" are used herein interchangeably to refer to a thin tubular member having a beveled end for insertion into an injection site on a subject. As used herein, the "distal" direction is in the direction toward the injection site, and the "proximal" direction is the opposite direction. "Axial" means along or parallel to the longitudinal axis of the needle and the "radial" direction is a direction perpendicular to the axial direction.

The invention is directed to an injection device and particularly to a needle hub assembly having a cannula with a predetermined length for penetrating the skin to a predetermined penetrating depth. The injection device has a skin contact surface for contacting and deforming the skin when the cannula penetrates the skin to assist in controlling the depth of penetration at various angles of injection with respect to the surface of the skin. The contact surface has a predetermined shape, width and height to control the depth of penetration into the skin to the desired layer of the skin.

The skin contact surface of the pen needle device surrounding the cannula has a width and height configured for providing greater control of the depth of penetration by the cannula. In one embodiment of the invention, the pen needle device is configured to obtain a cannula penetration of about 4 mm. The skin contact surface is further configured to control the shape, width and depth of deformation of the skin surface when the device is pressed against the skin during the penetration of the cannula. The width is determined as being the surface area that contacts the skin during the insertion of the cannula and during the injection or delivery of the drug using a normal insertion force. The height refers to the linear distance between the outer peripheral edge of the contact surface and the proximal end of the contact surface.

The injection device includes drug delivery device such as a pen needle device having an outer sleeve, a medicament cartridge sealed by a septum and a cap. A plunger is provided on the end of the cartridge to dispense the drug. The delivery pen has a structure and operation similar to those known in the art. A pen needle hub 10 is coupled to the injection device for delivering the drug to the patient. The pen needle hub 10 according to one embodiment of the invention shown in FIGS. 1-4 includes an outer cover 12, an inner shield 16, a needle hub 18 and a tear drop shaped tab 14 attached to the outer cover 12 to provide a sterile seal. The needle hub 18 includes a double-ended cannula 20 beveled and sharpened at both ends for coupling to the pen needle assembly and for penetrating the skin of the patient.

Figure 3:
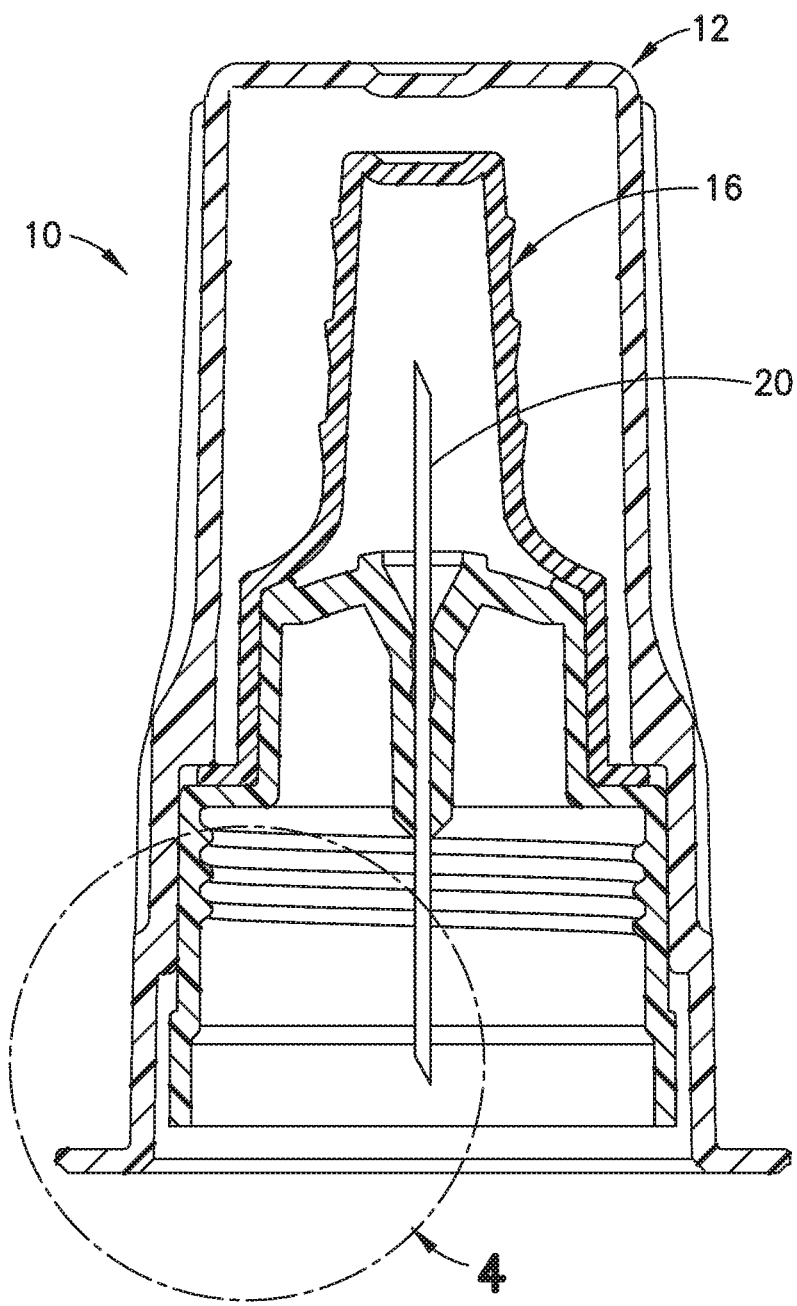
FIG. 3 is cross sectional side view of the needle hub assembly taken along line 3-3 of FIG. 2.
Figure 4:
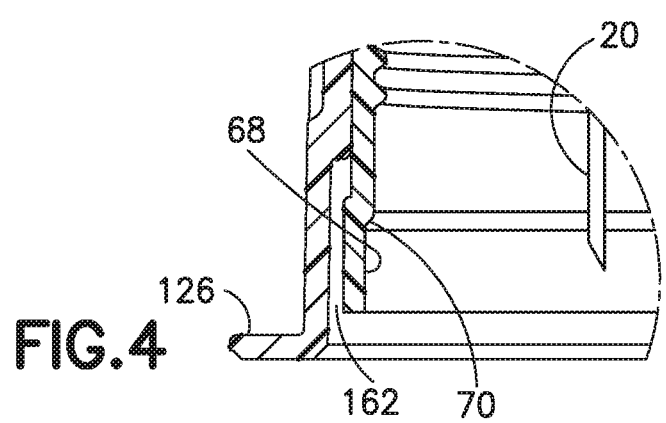
FIG. 4 is an enlarges cross sectional view of the bottom end of the outer cover and needle hub.
Figure 5:
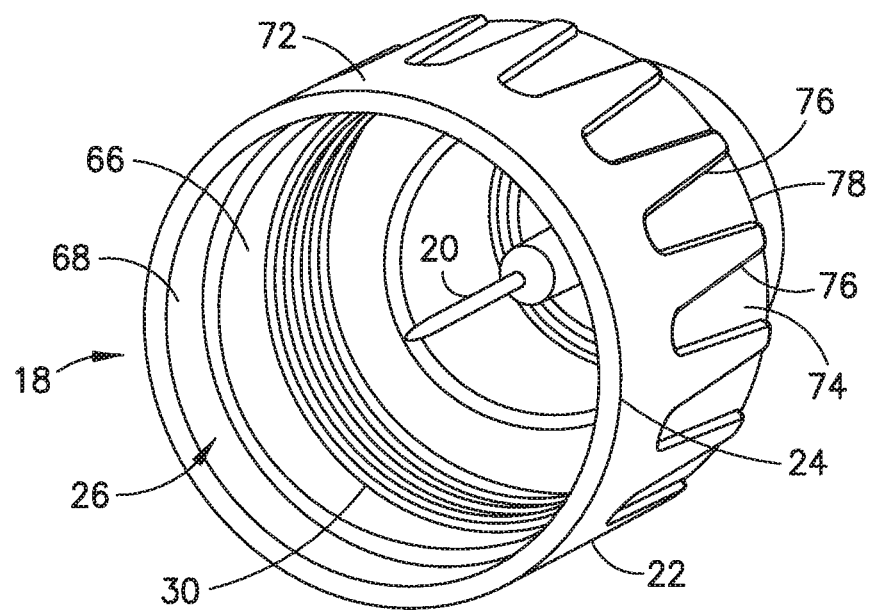
FIG. 5 is a bottom perspective view of the needle hub of FIG. 1.
Figure 6:
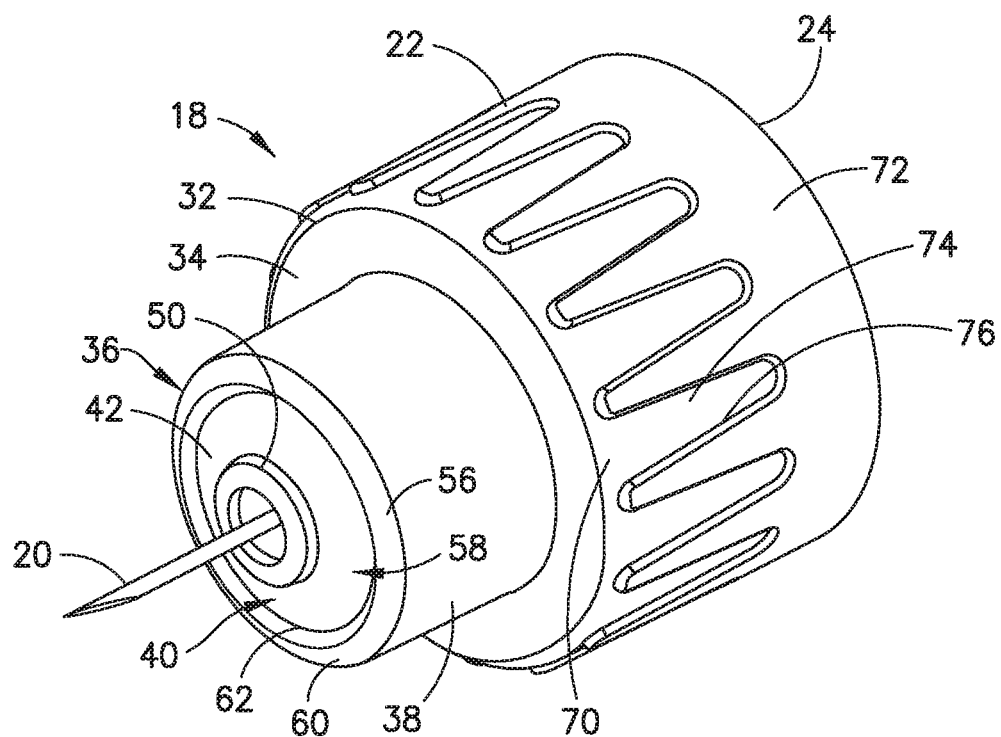
FIG. 6 is a top perspective view of the needle hub of FIG. 1.
Figure 7:
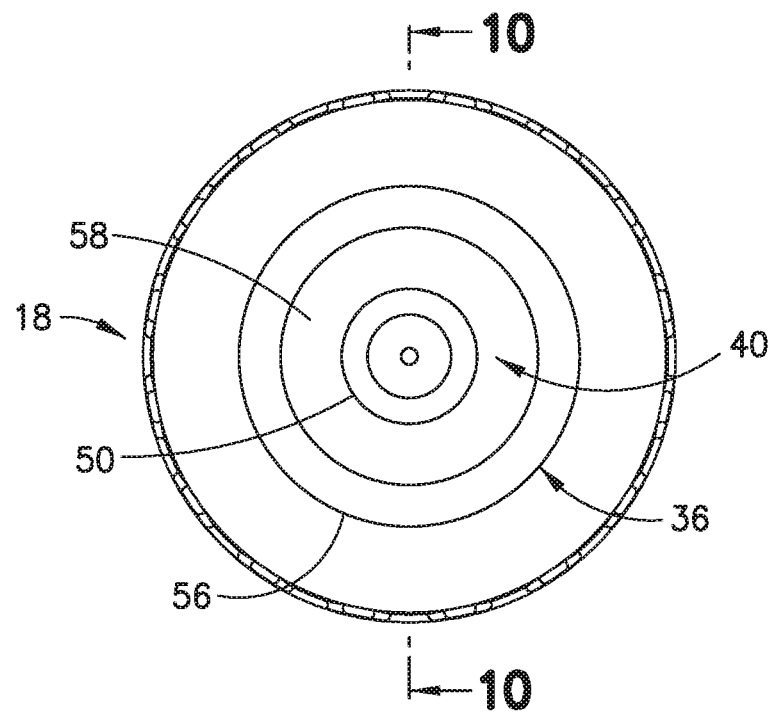
FIG. 7 is a top end view of the needle hub of FIG. 7.
Figure 8:
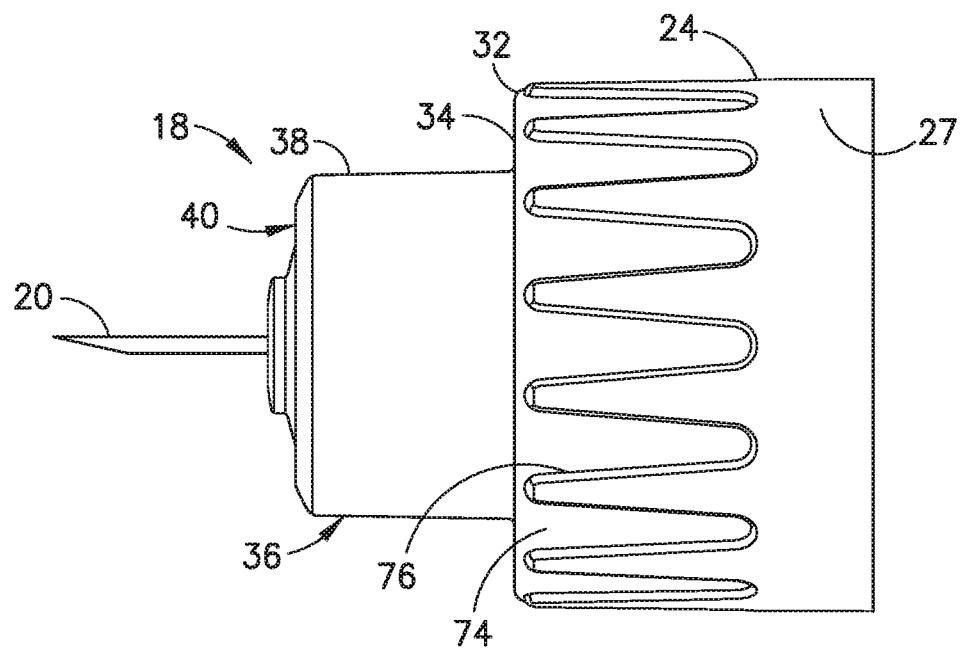
FIG. 8 is a elevational side view of the needle hub of FIG. 7.
Figure 9:
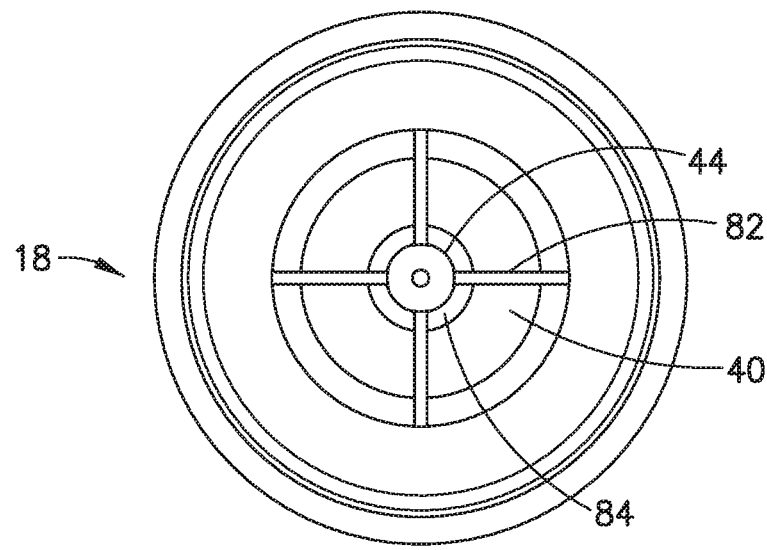
FIG. 9 is a bottom end view of the needle hub of FIG. 7.
Figure 10:
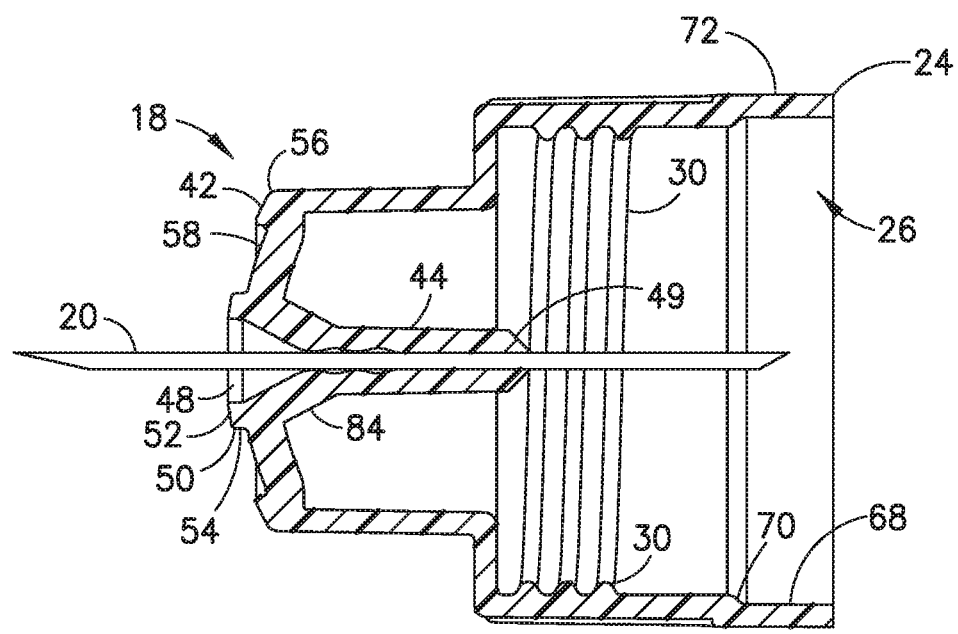
FIG. 10 is a cross sectional side view of a needle hub taken along line 10-10 of FIG. 7.

In the embodiment of FIGS. 5-10, the needle hub 18 for coupling to the delivery pen has a body 22 having a side wall 24 to form an open end 26. In the embodiment shown, body 22 has a substantially cylindrical shape. The open end 26 forms an internal cavity with internal threads 30 as shown in FIG. 3 and FIG. 10 for coupling to the pen needle delivery device. In another embodiment, the needle hub may be provided with flattened sides to assist in rotating the needle hub and coupling the needle hub to the pen needle assembly.

Body 22 of needle hub 18 has a distal end with a peripheral edge 32 forming a shoulder 34. The shoulder can be oriented in a plane substantially perpendicular to a central axis of the needle hub 18. A tower 36 forming an upper end portion of needle hub 18 extends from shoulder 34 in the direction of the central axis away from the open end 36. The tower 36 has a side wall 38 extending substantially parallel to side wall 24 of body 22 of needle hub 18. Tower 36 has an end wall 40 with a distal, axial face 42 forming a skin contact surface. End wall 40 can have a substantially convex shape. Axial face 42 can have a diameter of about 5 to 7 mm. The shoulder has a width to receive the inner shield and a width of about 1-4 mm from the peripheral edge of body 22 and side wall 38 of tower 36.

Figure 11:
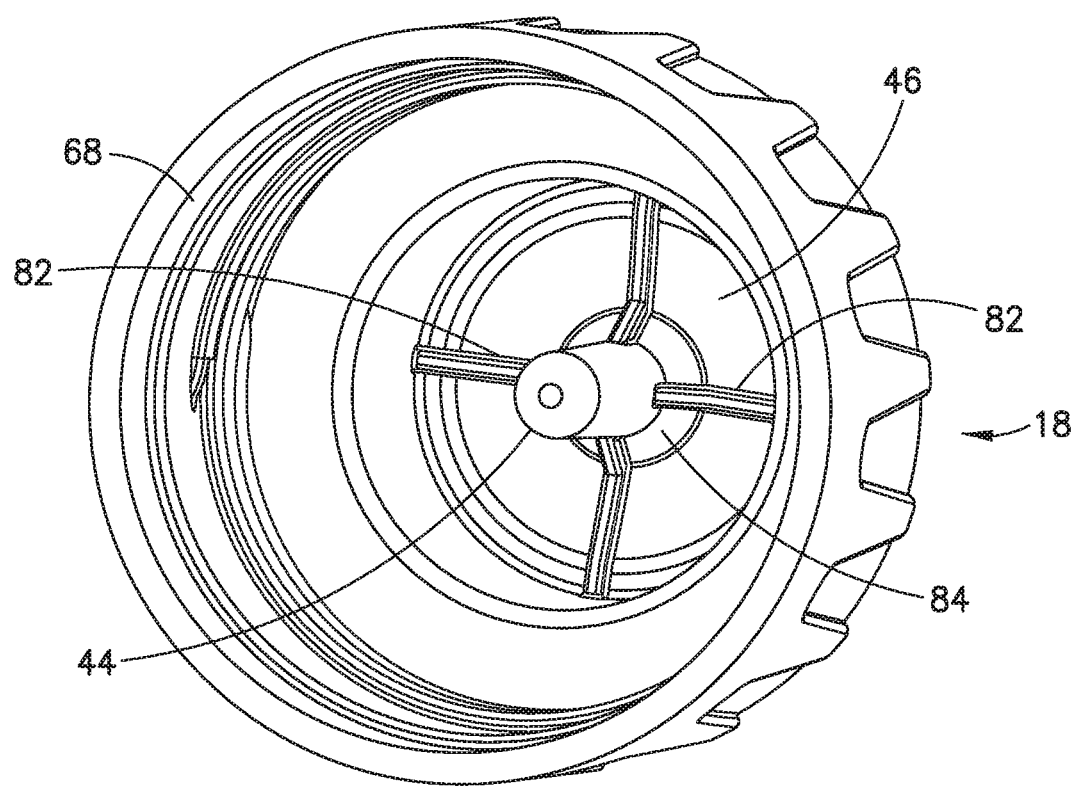
FIG. 11 is a bottom perspective view of the needle hub of FIG. 7.
Figure 12:
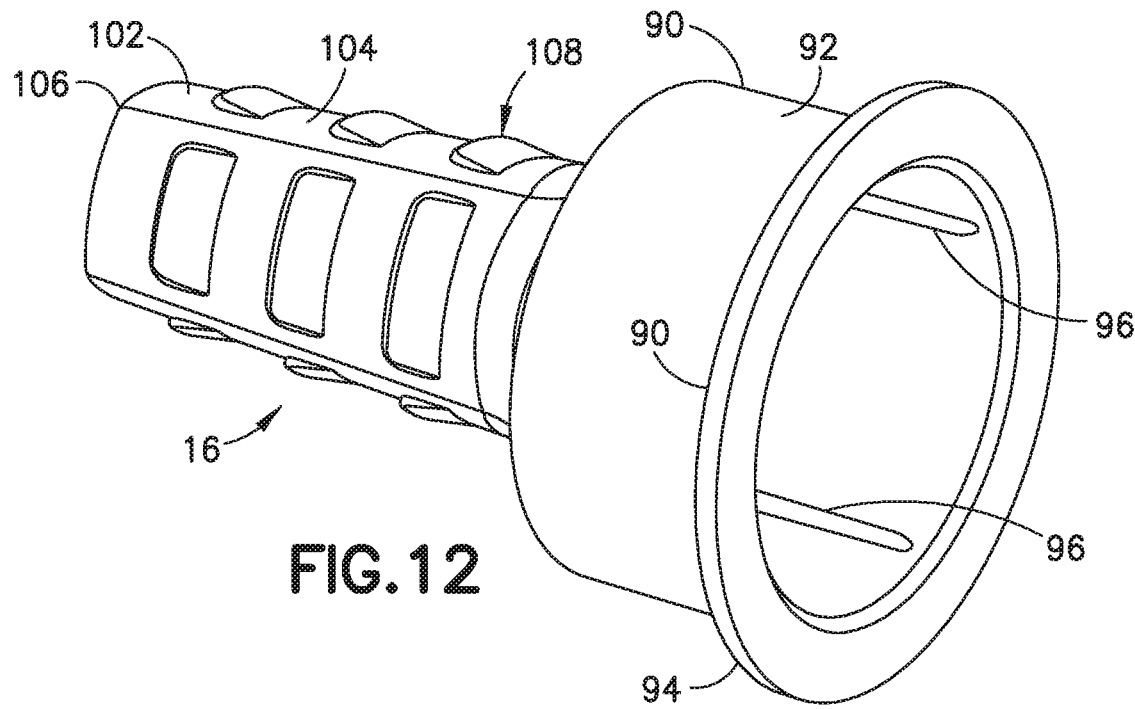
FIG. 12 is a bottom perspective view of the inner shield of FIG. 1.
Figure 13:
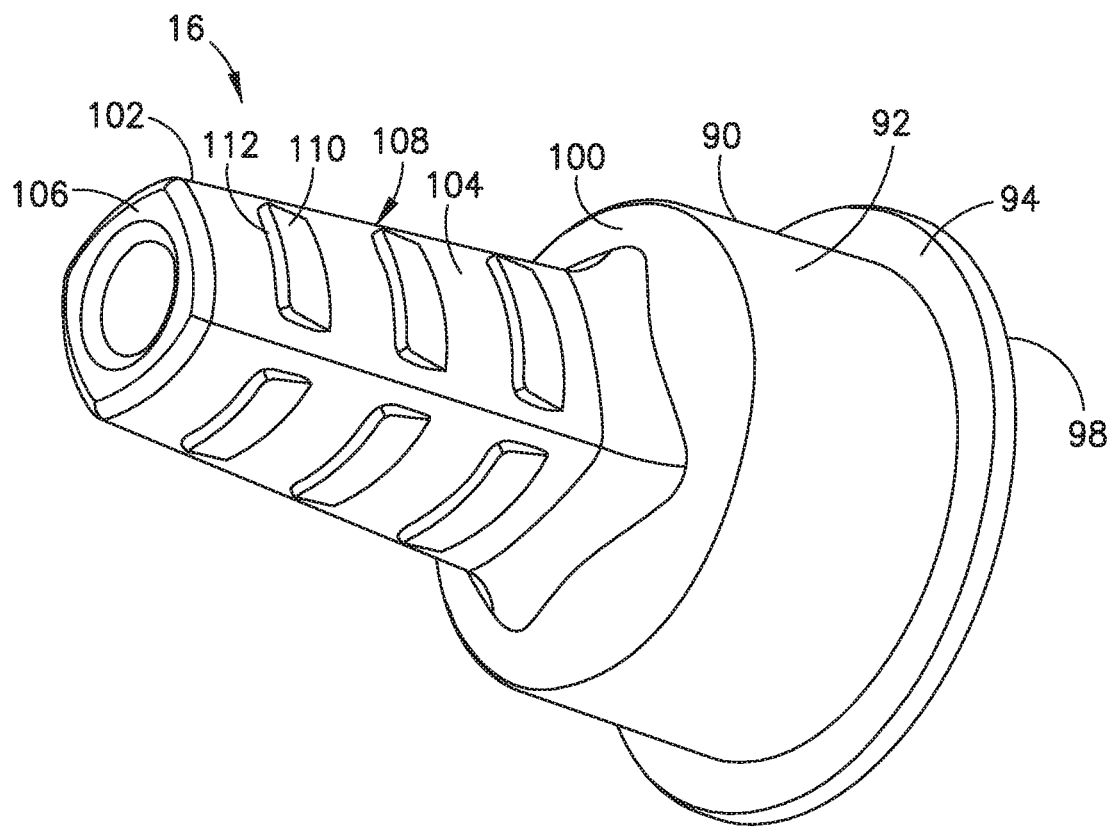
FIG. 13 is a top perspective view of the inner shield of FIG. 12.

A post 44 for supporting a cannula extends inwardly from an inner face 46 of end wall 40 of tower 36 as shown in FIG. 9-11. Post 44 projects inwardly in the direction of the center axis for supporting cannula 20. Post 44 has an axial passage extending through needle hub 18 for receiving the cannula and a conical shaped end 49. A well 48 is formed in end wall 40 at the distal face 42 for receiving an adhesive to couple cannula 20 to needle hub 18. In the embodiment shown, cannula 20 extends inwardly a distance for connecting the delivery device and extends outwardly from distal face 42 a distance for piecing the skin of the patient.

The needle hub 18 of FIGS. 5-10 deforms the skin by the insertion force during the insertion and penetration of the cannula by an insertion force normally applied by the patient. In the embodiment shown, the needle hub 18 has an inner ring 50 extending from the distal face 42 of tower 36. Inner ring 50 has an axially facing distal face 52 surrounding well 48 and cannula 20 with an inner side surface 54. An outer ring 56 is formed at the outer peripheral edge of tower 36 forming a recess 58 between inner ring 50 and outer ring 56. Outer ring 56 has an axially facing distal face 60 with an inner surface 62 facing inner side surface 54. In the embodiment shown, the surface of recess 58 and the axial faces of inner ring 50 and outer ring 56 have a substantially continuous, concentric radius of curvature and define the skin contact surface of needle hub 18. Recess 58 has a depth so that the skin of the patient deflects into the recess and contacts the bottom surface of the recess during needle insertion to deform the skin in a controlled manner. In one embodiment, the radial width of recess is substantially equal to the combined radial width of inner ring 50 and outer ring 58. The axial surface of the distal face of tower 36 has a convex dome shape where inner ring 50 is spaced axially outward relative to outer ring 56 and the axially facing surface of recess 58.

The initial penetration of the cannula 20 by the contact of the inner ring projecting from the tower 36 with the skin of the patient forms a depression in the skin and an initial cannula penetration depth. The surface of the skin then relaxes so that the surface of the skin conforms substantially to the shape of the contact surface formed by outer ring 56 and recess 58 and limits the depth of penetration of the cannula 20. The shape, surface area and height of the contact surface to provide control of the depth of penetration of the cannula during the insertion and penetration force being applied to the injection device.

Referring to FIGS. 9-11, side wall 24 of body 22 has an inner surface 66 at the proximal open end 26 of needle hub 22. In the embodiment shown, a recess 68 is formed in the inner surface 66. In one embodiment, recess 68 surrounds the circumference of needle hub 22 to form a continuous recess. Recess 68 extends a distance of side wall and terminates at an inclined beveled edge 70. Recess 68 can provide a larger open end to assist in assembling needle hub 18 to a delivery device.

As shown in FIG. 5-8 an outer surface 72 of side wall 24 includes a plurality of recesses 74 at the upper end forming a scalloped shape. Each recess 74 has a longitudinal length to cooperate with the outer cover 12 to assisting in rotating needle hub 18 and coupling to the pen needle assembly or other delivery device. Each recess 74 has a substantially V-shape formed by inclined sides 76 and an open top end 78. The recess 74 can provide the upper portion of the side wall with increased flexibility relative to a surface without recesses. Recess 68 in the bottom end of the side can provide a reduced thickness and flexibility similar to the flexibility provided by the recesses 74.

Referring to FIG. 9 and FIG. 10, inner face 46 of end wall 40 has a substantially conical shape corresponding to the shape of outer distal face 42. In the embodiment shown, end wall 40 has a substantially uniform thickness. Radially extending ribs 82 can be formed on inner face 46 of end wall 40 as shown in FIGS. 9-11. FIG. 11 is a bottom view showing ribs 82 extending between post 44 and an inner surface of side wall 38. For clarity, cannula 20 is not shown in FIG. 11 although it is understood that hub 18 will include cannula 20 during use. Post 44 has a conical shaped base portion 84 at the inner face 46 that converges to the cylindrical surface of post 44. In one embodiment, ribs 82 extend along the outer face of the conical portion 84 and the inner face 80. Ribs 82 have a width and axial height to increase the strength of end wall 40 and inhibit or reduce bending and deflection of end wall 40 during use.

During penetration of cannula 20, end wall 40 of tower 36 contacts the skin of the patient. Ribs 82 on inner surface 46 provide sufficient strength to end wall 40 to resist deflection and deforming of end wall 40 inwardly into the cavity and resist collapsing of the conical shape of end wall 40 when an excess insertion force is applied to the end wall 40. Ribs 82 also provide sufficient strength so that end wall 40 is sufficiently rigid to prevent an outward deflection or distortion of end wall 40 when a pulling force is applied that may cause failure of the adhesive and provide a predetermined pull force for removal of cannula. In the embodiment shown, four ribs 82 are provided although the number of ribs can vary depending on the stiffness of the end wall 40. The conical base 84 also provides stiffness to the end wall 40 to resist deflecting inward during use.

Figure 14:
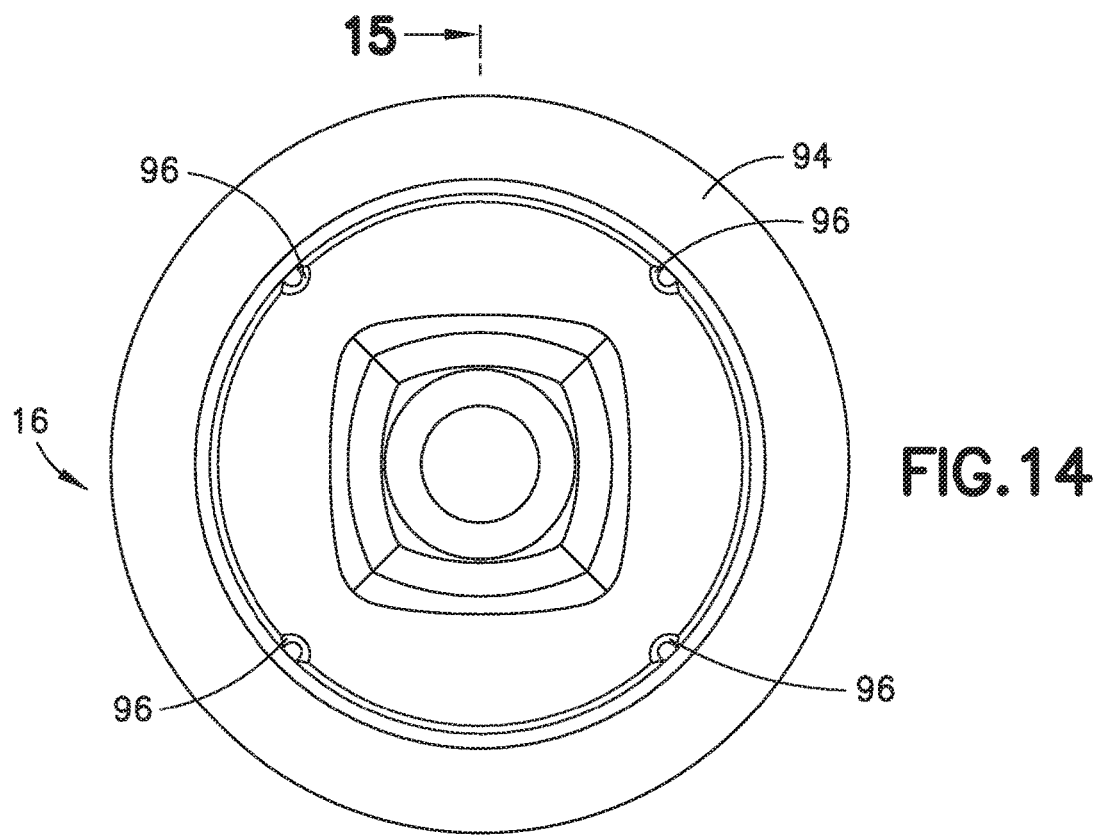
FIG. 14 is a bottom end view of the inner shield of FIG. 12.
Figure 15:
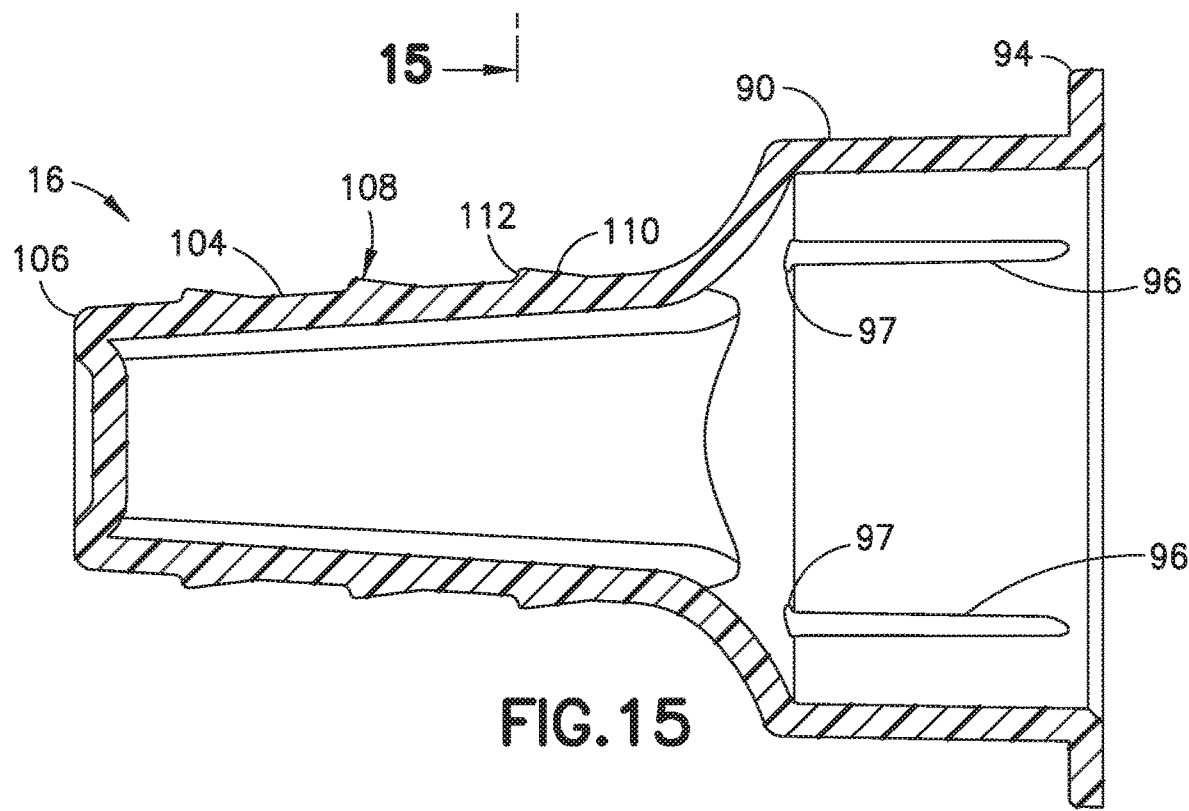
FIG. 15 is a cross sectional view of the inner shield of FIG. 12.

Referring to FIGS. 12-16, inner shield 16 has a length to receive cannula 20 and a width to cooperate with needle hub 18. Inner shield 16 as shown has a body 90 forming an end portion, a side wall 92 and a flange 94 extending radially outward from side wall 92 of body 90. Body 90 has a shape and an inner dimension complementing an outer shape and dimension of tower 36 of needle hub 18. Side wall 92 of body 90 has an inner surface for mating with the outer surface of side wall of tower 36. Internal ribs 96 extending in a longitudinal direction are formed on the inner surface of side wall 92 for gripping with the outer surface of tower 36 to provide a friction fit. Ribs 96 allow air to escape from the cavity of inner shield during assembly and disassembly to enable a controlled insertion and pull force with respect to needle hub 18. As shown in FIG. 15, an upper distal end of ribs 96 have an inwardly extending lip 97 to contact the shoulder 34 of needle hub 18 to limit insertion depth of needle hub 18 into inner shield 16. Flange 94 is oriented to mate with the shoulder 34 of body 22 as shown in FIG. 1. In the embodiment shown, flange 94 extends in a plane substantially perpendicular to a central axis of inner shield 16 and has a dimension defined by a peripheral edge 98 complementing the outer dimension of shoulder 34 and an outer dimension of side wall 24 of body 22 of needle hub 18.

Inner shield 16 includes a top wall 100 with a substantially concave outer surface and a conical shaped top end portion 102 extending axially from top wall 100 of body 90 with an internal dimension to receive cannula 20 when inner shield is coupled to needle hub 18 as shown in FIG. 1. Top end portion 102 in the embodiment shown, is defined by inclined side walls 104 that converge toward a distal end 106. Each wall has a slight convex curvature with a textured or gripping surface. In the embodiment shown, four walls are included to form a substantially square cross section. As shown in FIG. 14, side walls 104 have a width that decreases from body 90 to distal end 106. In other embodiments, top end portion 102 can have a rounded, cylindrical shape or tapered conical shape. Inclined side walls 104 have a gripping surface for assisting in the user gripping and removing inner shield 16 from needle hub 18 and placing inner shield back onto needle hub 18 after use. The gripping surface can be a roughened or textured surface portion or projecting members to assist in gripping and rotating inner shield 16 relative to needle hub 18.

Figure 16:
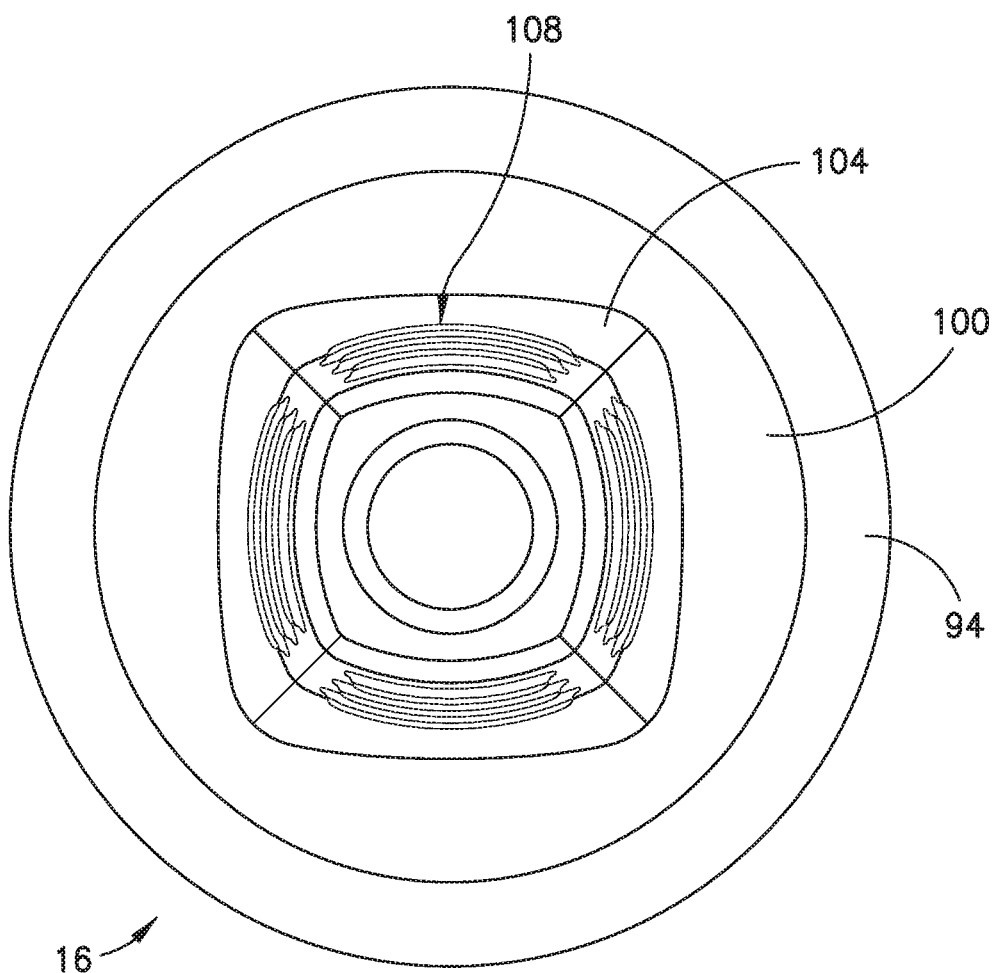
FIG. 16 is a top end view of the inner shield of FIG. 12.

In the embodiment shown, side walls 104 are formed with at least one, and typically a plurality of grips 108 spaced along the longitudinal length of each side wall 104. Grips 104 can be positioned at the distal end of the inner shield or spaced along the length of the inner shield. Grips 104 extend outwardly to allow the user to easily grip and rotate the inner shield when removing the inner shield from the needle hub 18. In the embodiment shown three grips 108 are provided on each side wall 104. In other embodiments, more than three or fewer than three grips can be provided. Grips 108 in the embodiment shown have an inclined major face 110 and an inclined minor face 112. Major face 110 is inclined outwardly toward distal end 106 and has a surface area sufficient to be gripped by the user. Minor face 112 is inclined toward body 90 of inner shield 16. As shown in FIG. 16, grips 108 have a decreasing width with the decreasing width of each side wall toward distal end 106.

Outer cover 12 has a shape and dimension to complement the shape and dimension of inner shield 16 and needle hub 18. Outer cover 12 has a body 120 with a side wall 122, a bottom end forming an open end 124 for receiving inner shield 16 and needle hub 18. A flange 126 extends radially outward from the bottom end. Flange 126 is oriented to mate with flange 94 of inner shield 16 and shoulder 34 of needle hub 18. In the embodiment shown, flange 126 has a peripheral edge 128 defining a radial dimension complementing the outer dimension of needle hub 18. The open end of outer cover 12 includes a beveled or chamfered edge 160 extending from a bottom face of flange 126 to the inner surface of side wall 122.

Side wall 122 of body 120 terminates at a top end 130 and converges inwardly to form a conical shaped axial face 132. A top section 134 forming a top end having a side wall 136 extends from conical shaped face 132 to a distal end 138. A plurality of ribs 140 extend radially outwardly in a longitudinal direction from an outer surface of side wall 136. An inner surface 142 of side wall 136 includes indicia, such as at least one and typically a plurality of ribs 144. Ribs 144 can be provided to resist crushing or deflection of outer cover 12 during removal and assembly. In the embodiment shown, ribs 144 extend around the inner surface 142 and are oriented substantially perpendicular to the longitudinal axis of outer cover 12. Three ribs 144 are shown aligned and spaced apart around the inner surface to provide strength to the side wall 122 during use.

In one embodiment, ribs 144 provide indicia to define a predetermined volume in the end of the outer cover 12. During use, the pen needle can be actuated to deliver a medication into the outer cover to measure the dosage delivered by the pen needle using the ribs as indicia to measure the volume and accuracy of the delivery device. In other embodiments, other forms of indicia can be used to mark a predetermined volume in the outer cover.

Figure 17:
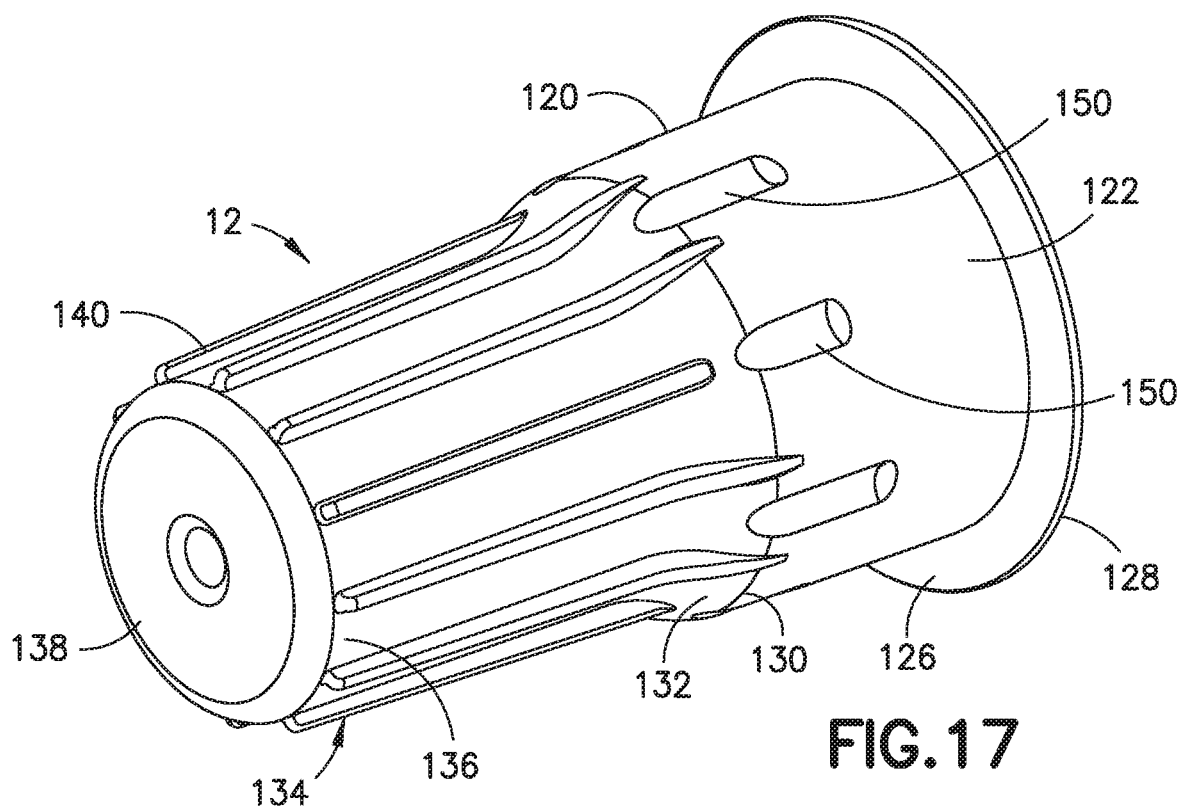
FIG. 17 is a top perspective side view of the outer cover of the needle hub of FIG. 1.

Referring to FIG. 17, side wall of 122 of body 120 includes at least one and typically a plurality of detents 146 extending from an inner surface 148 in a longitudinal direction with respect to the center axis of outer cover 12. Detents 146 are oriented to mate with recesses 74 of needle hub 18 during assembly to enable rotating of needle hub 18 by rotation of outer cover 12 during coupling and removing needle hub 18 from a pen delivery device. The inclined sides 76 of the respective recess 74 provide an enlarged open end of the recess to receive the detents 146. In the embodiment shown in FIGS. 17-21, eight detents 146 are provided, while in other embodiments four detents are provided.

Detents 146 are formed by molding recesses 150 on an outer face 152 of side wall 122. As shown in FIG. 17, recesses 150 extend in a longitudinal direction at a top end of side wall 122 and form an open end in the conical face 132. Detents 146 have a length to mate with the recesses 74 while allowing needle hub 18 to be received in outer cover 12 as shown in FIG. 1 so that a bottom edge of needle hub 18 is recessed within the cavity of outer cover 12. In one embodiment, one or more of the detents have an inclined end to assist in guiding the detents into the respective recess 74. In the embodiment shown, alternating detents 146 have a longer length than the adjacent detents to engage the corresponding recess 74 in needle hub 18 to align all of the detents with a respective recess by positioning outer cover 12 on needle hub 18. The longer detents having an end closer to the bottom edge of needle hub 18 than the adjacent detents have an inclined or angled end face forming a point to pass easily into the recess 74.

Figure 18:
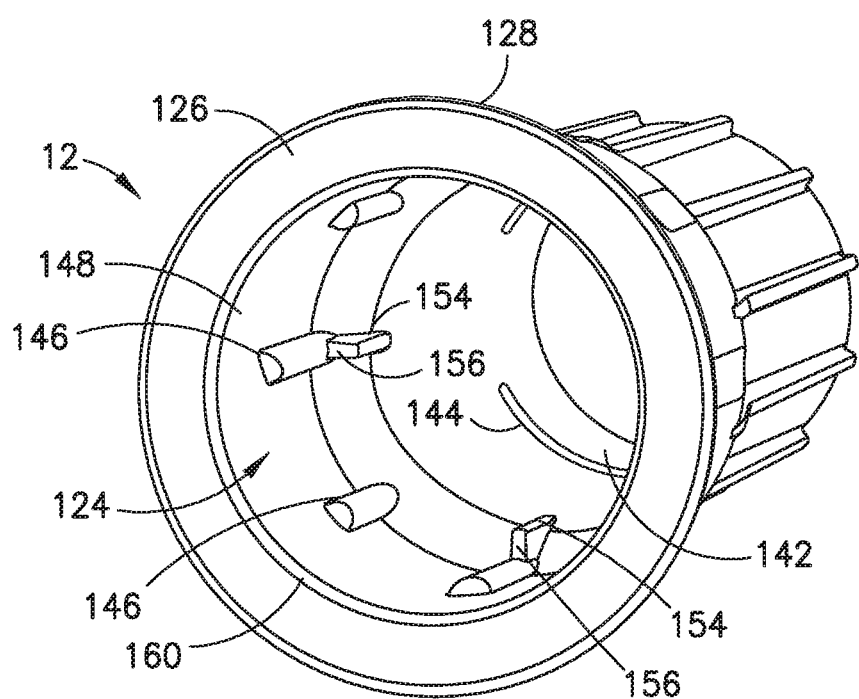
FIG. 18 is a bottom perspective view of the outer cover of FIG. 17.
Figure 19:
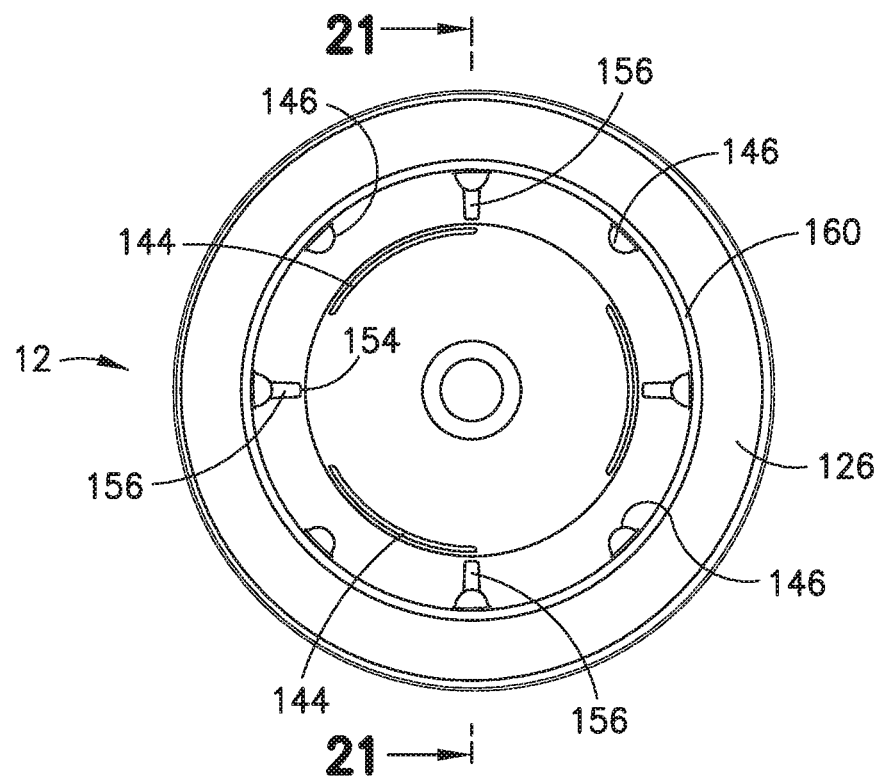
FIG. 19 is a bottom view of the outer cover of FIG. 17.
Figure 20:
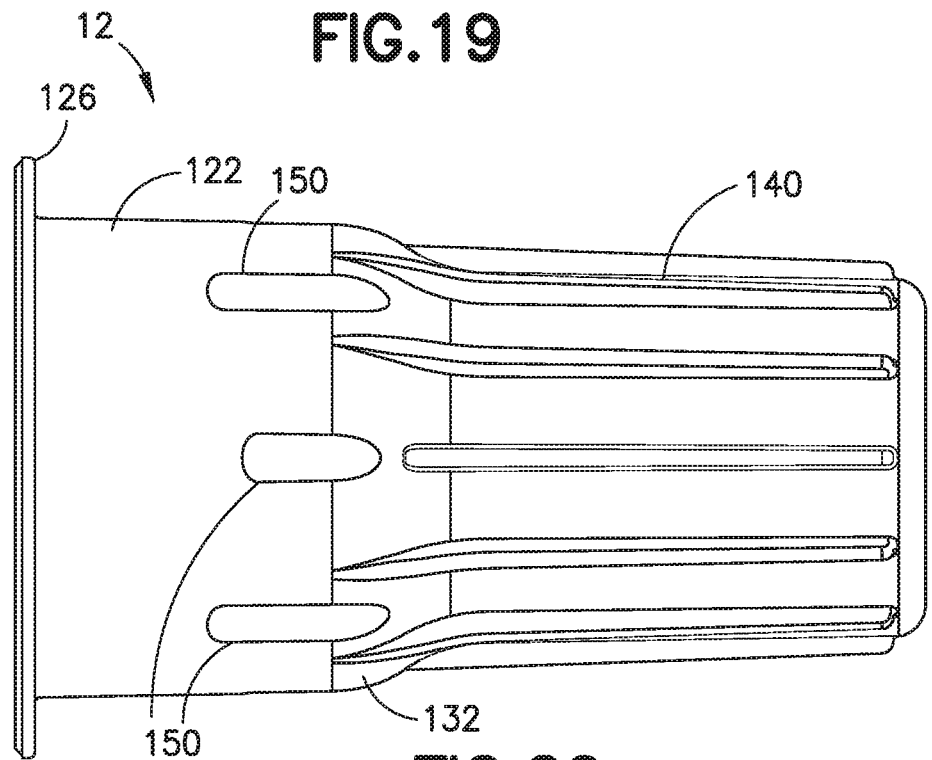
FIG. 20 is an elevational view of the outer cover of FIG. 17.
Figure 21:
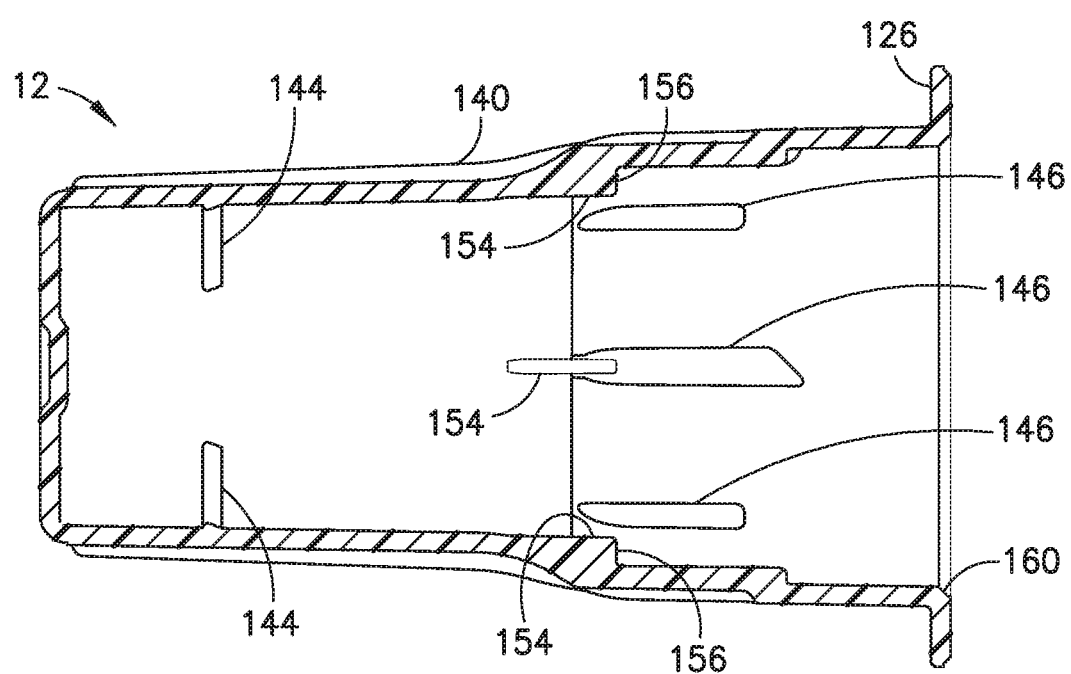
FIG. 21 is a cross sectional side view of the outer cover of FIG. 16.

As shown in FIG. 18 at least one stop member 154 is formed on the inner face 148 to limit the depth of inner shield 16 and needle hub 18 into the cavity of outer cover 12. Stop member 154 is formed at an upper end of side wall 122 and has a downwardly facing surface 156 positioned to contact a top face of flange 94 of inner shield 16 or a top face of shoulder 34 of needle hub 18. Stop member 154 can be formed with one or more detents 146 as shown in FIG. 18. In the embodiment shown, four detents are provided and spaced radially around the inner surface of the side wall 122 a substantially uniform distance.

The needle hub assembly 10 of the invention is assembled in the manner shown in FIG. 1. Inner shield 16 is positioned on the top end of needle hub 18 where flange 94 of inner shield 16 contacts shoulder 34 of needle hub 18. Outer cover 12 is then placed over inner shield 16 and needle hub 18 where stop member 154 contacts the top face of flange 94 of inner shield 16 to capture inner shield between needle hub 18 and outer cover 12. Detents 146 on outer cover 12 mate with the recesses 74. In the embodiment shown, needle hub 12 is recessed slightly from the bottom face of flange 126 and the chamfered edge 160. The detents 146 contact the outer surface of side wall 38 of needle hub 18 to form an annular gap or recess 162 between outer cover 12 and needle hub 18.

Tab 14 is attached to the open end of outer cover 12 to seal the assembly. In one embodiment of the invention, tab 14 has a substantially tear drop shape to assist the user in removing the tab 14 from the outer cover to expose the needle hub 18. Tab 14 can include a thermoplastic film for heat sealing to the open end of outer cover 12. The thermoplastic film has a thickness to ensure complete sealing of outer cover 12 to provide a sterile seal. The thermoplastic film can have a thickness such that a portion of the thermoplastic under the sealing and bonding pressure may flow outwardly or inwardly from the bottom face of the flange 126. The recess 162 formed between the needle hub 18 and outer cover 12 and the recess formed by the chamfered edge 160 can receive the excess flow of thermoplastic material to prevent the thermoplastic material from contacting needle hub 18 and prevent interference with the removal of needle hub 18 from outer cover 12.

The skin contact surface formed by the distal face 42 has a substantially convex or conical shape forming a continuous and uniform curvature extending from the outer edge of tower 36 of needle hub 18 to the distal end or outermost portion of the contact surface of the needle hub and the cannula 20 so that the skin contact surface has a substantially semispherical or dome shape that contacts the skin during penetration of the cannula and delivery of the drug. The convex surface of the skin contact area can have a width or diameter of greater than 3.0 mm and typically about 6.0 to 8.0 mm and a height of about 0.5 to about 1.5 mm measured from the outer peripheral edge of the contact surface to the outermost center portion of the contact surface surrounding the cannula and spaced axially from the peripheral edge. In one embodiment the convex skin contact surface has a height of about 1.0 mm and a diameter of about 7.0 mm. The convex surface can have a radius of curvature of 6.0 to 16.0 mm. In various embodiments of the invention, the convex surface has radius of curvature of 6.0 to 9.0 mm. In other embodiments, the convex surface can have a radius of curvature of 6.0 to 7.0 mm. In one embodiment, the convex contact surface has a radius of curvature equal to or greater than the diameter of the contact surface. The radius curvature can be about 1 to 1½ times the diameter of the contact surface.

The ratio of the diameter (D) to the height (H) of the contact surface influences the depth of penetration of the cannula on insertion into the skin. Generally, the larger the ratio provides more surface area that will contact the skin and greater control of the depth of penetration. A smaller ratio D:H provides a smaller surface area that can compress the skin on insertion and result in a deeper penetration of the cannula. In certain embodiments, the ratio of the diameter to the height of the surface area can range from about 2:1 to 10:1. In other embodiments the ratio can range from about 5:1 to 8:1.

The above description of the preferred embodiments is not to be deemed as limiting the invention, which is defined by the appended claims. The disclosure is intended to enable the artisan of ordinary skill to practice variants of the invention described without departing from the scope of the invention. Numerical limitations herein, in the specification and in the claims, are understood to be limited by the modifier "about," such that minor departures yielding equivalent results is within the scope of the invention. Features or dependent claim limitations disclosed in connection with one embodiment or independent claim may be combined in another embodiment or with a different independent claim without departing from the scope of the invention.

What is claimed is:

1. A pen needle assembly comprising:
   a needle hub having an open end for coupling with a delivery pen for delivering a medication, a distal end opposite said open end, and a cannula extending from said distal end;
   an inner shield having a body with an open end for coupling to said needle hub; and
   an outer cover having a body with an open end for coupling to the needle hub, an upper section extending from said body of said outer cover and having an outer surface with an external gripping surface, a plurality of detents projecting inwardly from an inner surface of said body of said outer cover and oriented for mating with an outer surface of said needle hub, and a plurality of spaced apart stop members projecting inwardly from a respective detent and oriented to contact said inner shield when said outer cover is positioned on said needle hub.

2. The pen needle assembly of claim 1, wherein said needle hub comprises;
   a body having a sidewall with an outer surface having a plurality of recesses at an upper end of said side wall oriented for mating with a respective detent on said outer cover, an inner surface defining a first inner dimension for mating with the delivery pen, and a recess formed on said inner surface at said open end; and
   a tower extending from said body of said needle hub and having a sidewall spaced inwardly from said side wall of said body of said needle hub, and an end wall defining a skin contact surface, and where said cannula extends from said end wall.

3. The pen needle assembly of claim 2, wherein said end wall of said tower has an inner surface with at least one radially extending strengthening rib.

4. The pen needle assembly of claim 1, wherein
said inner shield has a top wall at a top end of said body of said inner shield, and
a top end portion extending from said top wall of said inner shield and having an inner dimension less than an inner dimension of said body of said inner shield, said top end portion having an outer surface with a textured portion to define a gripping surface.

5. The pen needle assembly of claim 4, wherein said textured portion is defined by a plurality of projecting members.

6. The pen needle assembly of claim 4, wherein
said body of said inner shield has at least one internal rib extending in an axial direction with respect to said inner shield.

7. The pen needle assembly of claim 1, wherein said inner cover has a flange extending radially outward from a proximal end of said inner cover, and said stop members on the inner surface of said body oriented to contact said flange of said inner shield when said outer cover is positioned on said needle hub.

8. A pen needle assembly of claim 1, wherein
said needle hub has a body having a sidewall with an outer surface with an outer dimension, and an inner surface, said outer surface having a plurality of recesses extending from a top end of said side wall and extending toward said open end, a bottom end of said side wall having a thickness less than a thickness of said top end of said side wall;
a tower extending from said body of said needle hub and having a sidewall with an outer surface, an inner surface, and said tower having an outer dimension less than said outer dimension of said body, and an end wall defining a skin contact surface; and
a post extending from an inner surface of said end wall of said tower and extending toward said open end of said body, said post configured for supporting a cannula extending from said end wall of said tower.

9. The pen needle assembly of claim 8, wherein
said bottom end of said inner surface of said side wall of said body of said needle hub includes a recess extending around said open end to define a substantially uniform thickness at said bottom end.

10. The pen needle assembly of claim 8, wherein
said end wall of said tower has an inner surface with a plurality of ribs projecting into a cavity of said needle hub and extending between said side wall of said tower and said post.

11. The pen needle assembly of claim 10, wherein
said post has a conical base portion at said inner surface of said end wall, and where said plurality of ribs are formed at least partially on said conical base portion.

12. The pen needle assembly of claim 10, wherein
said outer face of said end wall of said tower includes an outer ring at an outer edge of said end wall and having an axial face that is inclined with respect to a center axis of said needle hub, and an inner ring at the center portion of said end wall and having an axial face spaced outwardly from said outer ring with respect to the center axis, said inner ring and said outer ring defining a skin contact surface and defining a recess between said inner ring and outer ring.

13. The pen needle assembly of claim 1, wherein
said stop members are integrally formed with a respective detent and have an axial face to contact said inner shield, and where said stop member are formed at a distal end of the respective detent.

14. The pen needle assembly of claim 13, wherein
said inner shield has an outwardly extending flange having an outer dimension complementing an outer dimension of the needle hub and where said axial face of said stop member contacts a top surface of said flange.

15. The pen needle assembly of claim 1, wherein
said inner shield has an upper section with a plurality of substantially flat outer side surfaces converging to a distal end and having a plurality of projecting members extending outwardly from said side surface gripping surface.

16. The pen needle assembly of claim 1, wherein
said inner shield has a top end portion with at least two opposite facing, substantially flat side surfaces, each of said side surfaces having a plurality of grip members forming a gripping surface for gripping by a user.

17. The pen needle assembly of claim 16, wherein
said grip members have an outer surface that is inclined with respect to a center axis of said inner shield.

18. The pen needle assembly of claim 16, wherein
said body of said inner shield has an outwardly extending flange having an outer dimension complementing an inner dimension of said body of said outer cover, and where said top end portion of said inner shield has a substantially square cross-section.

19. The pen needle assembly of claim 16, wherein
said top end portion of said inner shield is tapered to define a substantially conical shape, and where an inner surface has at least one inwardly projecting rib extending an axial direction with respect to the center axis of said inner shield, each said rib having an inwardly extending lip at a distal end of said rib oriented for contacting an axial facing surface of said needle hub.

* * * * *